United States Patent [19]
Tischlinger

[11] 3,978,858
[45] Sept. 7, 1976

[54] GLASS TUBE AND THERMOPLASTIC RESIN FINGER GRIP SLEEVE ASSEMBLY

[75] Inventor: Edward A. Tischlinger, Des Plaines, Ill.

[73] Assignee: MPL, Inc., St. Louis, Mo.

[22] Filed: Mar. 18, 1974

[21] Appl. No.: 451,962

Related U.S. Application Data

[62] Division of Ser. No. 197,717, Nov. 9, 1971, Pat. No. 3,803,700.

[52] U.S. Cl. .............................. 128/237; 128/218 P; 128/234; 222/386; 264/292
[51] Int. Cl.² ......................................... A61M 1/00
[58] Field of Search ....... 128/218 N, 218 D, 218 M, 128/215, 218 P, 218 PA, 218 R, 218 C, 234, 235, 237, 238, 261, 218 NV; 215/246, 317; 222/386; 264/271, 291, 292

[56] References Cited
UNITED STATES PATENTS

| | | | |
|---|---|---|---|
| 2,043,832 | 6/1936 | Kratz | 128/215 |
| 2,591,706 | 4/1952 | Lockhart | 128/218 D |
| 2,648,334 | 8/1953 | Brown et al. | 128/218 D |
| 2,707,466 | 5/1955 | Hoskins et al. | 128/218 D |
| 2,854,975 | 10/1958 | Cohen | 128/218 N |
| 3,108,592 | 10/1963 | Hassing et al. | 128/218 N |
| 3,366,286 | 1/1968 | Kloehn | 222/386 |
| 3,417,904 | 12/1968 | McLay | 128/218 C |
| 3,473,646 | 10/1969 | Burke | 128/220 X |
| 3,612,320 | 10/1971 | Wassilieff | 215/317 X |
| 3,699,961 | 10/1972 | Szpur | 128/218 M |
| 3,735,761 | 5/1973 | Hurschman et al. | 128/218 DA X |

*Primary Examiner*—John D. Yasko
*Attorney, Agent, or Firm*—Kinzer, Plyer, Dorn & McEachran

[57] ABSTRACT

A glass tube and thermoplastic resin finger-grip sleeve assembly in which the finger-grip sleeve is cam-stretched onto and frictionally retained on a glass tube, which is a section of die-formed glass tubing. Increase in latitude of operable interference fit and stretch is effected by assembling the finger-grip sleeve in a heated condition.

5 Claims, 5 Drawing Figures

GLASS TUBE AND THERMOPLASTIC RESIN FINGER GRIP SLEEVE ASSEMBLY

This is a division of application Ser. No. 197,717 filed Nov. 9, 1971 now U.S. Pat. No. 3,803,700.

This invention relates to a tube and finger-grip assembly for use in combination liquid containment and dispensing assemblies, particularly syringe assemblies, for packaging and dispensing of liquid drugs and other pharmaceutical chemicals, and relates more particularly to a glass tube and thermoplastic resin finger grip sleeve assembly for such use and purposes, a successful thermoplastic resin having been found to be polypropylene.

It has been common in the syringe art to provide syringes formed from both glass and plastic members. It is known that glass syringes have an important advantage of providing a clear and chemically inert container for drugs and other chemicals which are desired to be injected. The transparency of the glass enables the ready detection of any visible foreign particulate matter, and in addition the relatively chemically inert characteristic of syringe glass materials enables the injectable drug or chemical to be left in contact with the glass walls of the container for substantial periods of time without altering the chemical properties of the drug by combination with chemicals in the syringe material or by evaporation through the container wall of various chemical constituents in the drug or other chemical liquid. Thus, it is a particular advantage to be able to employ the advantageous properties of glass when packaging and storing drugs over a long period of time. Typically, a type of glass known as Type I or boro-silicate glass, is used for this purpose, having a high order chemical inertness. However, this type of glass is somewhat difficult to handle in manufacturing a syringe by forming operations on a glass tube, and as a syringe formed with its entire body of glass requires the opposite ends of the glass body to be formed to provide finger-grip flanges at one end and a nose tip at the opposite end or to adhere glass end pieces thereto, for dispensing and attachment to further units such as a hypodermic needles, or for use simply for dispensing it will be readily appreciated that such all-glass syringe bodies are troublesome and expensive to manufacture, and have other substantial drawbacks, including that of ease and danger of breakage of the end formed or secured sections, as in so forming or securing, stresses are set up in the glass, and weak spots are developed which cause the syringe to be subject to breakage at these points. This is a particularly important hazard for the finger-grip flange section, as breakage at this point may cause cutting of an operator and/or the patient. In addition, the breakage may take place in the course of handling the syringe body after formation of the flange and nose tip ends thereon, as in the course of filling the syringe, inserting a plunger piston therein, printing of the syringe body, etc. However, a special hazard is the possibility of the flange breaking during use, as all-glass syringes have been known to cause serious finger cuts due to breakage of the flange when pressure is applied during the actual injection procedure. Thus, there are two major disadvantages in the use of all-glass syringes, namely the high cost of providing the flange and nose tip end, and the hazard of breakage.

These two disadvantages of cost and breakage hazards are readily overcome by the use of plastic syringes, and particularly injection-molded plastic syringes and syringe body components; however, all-plastic syringes have been found generally unsuitable for storage of drugs and other active chemicals, and therefore are unusable for a prefilled syringe. The chemical makeup of substantially all thermoplastic and thermosetting resins is such that there is an appreciable chance of the contained drug combining with chemicals in the plastic, or in other instances the plastic may act in an absorptive fashion, having a tendency to absorb the chemicals out of the drug into the plastic, thus changing the chemical constituency and for relative proportions of the drug or other chemical liquid contained in the plastic syringe body. In addition, it is also well known that all thermoplastic resins have a moisture vapor transmission characteristic which can cause an undesired loss of fluid during long periods of storage.

In a third type of prior art syringe arrangements related to this problem, a tubular glass element has been attempted to be used with thermoplastic resin parts assembled to the glass. In such known arrangements, the thermoplastic resin parts have been secured to the glass by use of adhesives. However, adhesive securing is slow, messy, and provides an undesirable opportunity for the adhesive material to subsequently come into contact with the contained drug or other liquid chemical, which would of course endanger the chemical purity of the drug. In addition, while it might be possible to form a plastic member onto a glass tube, through an insert mold process, such insert mold process requires very close tolerance controls, which would not normally be available when employing commercially available glass tubing, which is supplied with a fairly wide tolerance variation. Screw-on mechanical connections between a glass tube and a plastic member are generally less than wholly advantageous, as the formation of such threads on the glass tube create an expense, and in addition create stress conditions which may cause breakage, as well as require a close tolerance control to effect an effective seal in those instances where sealing may be required. While snap-over lip-type plastic cover caps have been employed in various fashions to fit over a beaded glass mount, such as a bottle mouth, such snap-over cap lip connection arrangements are not at all satisfactory for syringe construction, as the interference snap fit interconnection formed thereby is short and does not provide sufficient retentive resistance to pull-off forces to enable its satisfactory use for glass tube and plastic finger grip or nose piece connections in syringe use assemblies. Minimal reliable pull-off force resistance of the order of approximately 5–8 pounds and more is often necessary, and higher orders of resistance are desirable for insured reliability.

It is accordingly a feature of the present invention to overcome the disadvantages of the prior art described above, by utilizing the advantages of glass tube as a drug or other chemical storage container, while utilizing the inexpensive and reliable mechanical properties of an injectable thermoplastic resin for the finger grip section of a tube and finger grip assembly which may be readily employed as a filling container and as a subcombination constituent portion of a syringe. This assembly is particularly advantageous in enabling ease of mechanical handling of the glass tube, both before and after assembly with the plastic flange, during the various manufacturing operations performed thereon, including washing, feeding, sterilizing and printing of graduations or legends thereon, without the substantial disadvantages afforded in such handling and processing operations which are encountered when the tube has a glass flange formed thereon. In addition, it will be appreciated that by employment of the glass tube as the body portion in the subsequent forming a syringe, the open-ended glass tube may be readily utilized to contain a desired drug or other chemical liquid without necessity for the liquid to come into contact with the plastic flange during an extended storage period. In such arrangement, the opposite ends of the glass tube may be suitable sealed off during the storage period, and a suitable ancillary dispensing/connector nose member may be secured as may be desired at the end of the glass tube opposite to the plastic finger grip member. The seals and nose and arrangements are not a part of the present invention, and an example of such is therefore not described herein, it being appreciated that various constructions and arrangements may be utilized within the scope and intent of the present invention.

In effecting my invention, various thermoplastic resins have been attempted to be employed, and great difficulty has been encountered in attempting to resolve this problem, as the various thermoplastic resins have been found to exhibit various difficulties, including cracking or rupturing of either the finger grip tube engaging portion or breakage of the glass, insufficient retention, resistance, inadequate elasticity with sufficient retention capability, too much flexibility, and long- and short-term creep, with resultant long- and short-term cracking and/or loosening. However, by practicing the unique method according to the present invention, and by careful selection of parameter limits for the glass tube and thermoplastic resin finger grip, I have been able to successfully form a glas tube and thermoplastic resin finger grip assembly which may be simply and reliably manufactured and utilized. A particular thermoplastic resin material which I have found usable in practicing my method is polypropylene.

The present invention is therefore directed to a glass tube and thermoplastic resin finger grip sleeve asembly, the details of which are described in the course of the following description of the invention.

Still other objects, features and attendant advantages will become apparent to those skilled in the art from a reading of the following detailed description, taken in conjunction with the accompanying drawings wherein.

Figure 1:
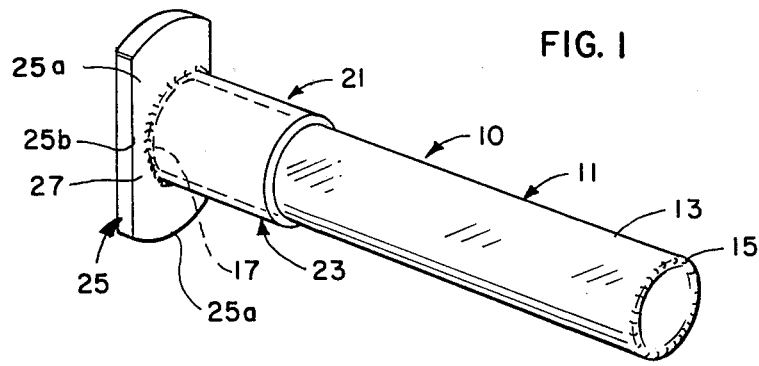
FIG. 1 is a perspective view of a preferred embodiment constructed in accordance with the invention.

Referring now in detail to the fingers of the drawing, a tube and finger grip sleeve assembly 10 includes a glass tube 11 formed of a length of straight cylindrical tubing which may be conventionally formed by a die-formed melt process, and subsequent cutting into sections to form desired lengths of glass tubing to be utilized for the glass tube 11. Glass tube 11 includes a straight cylindrical tubular wall 13, which is preferably fire-polished at its opposite ends 15 and 17 to form a fire-polished bead thereon. As an alternative, the opposite ends may be lightly or heavily beveled at their outer annular edge as by grinding or sanding. The fire-polished beads 15a and 17a, at the respective tube ends 15 and 17, may be conventionally formed, and preferably are relatively small, adding on the order of 0.001–0.005 inch diameter to the external diameter of the glass tube, although greater bead size formations may be utilized for given end uses, particularly where internal diameter restrictions are not critical or of material importance. Likewise, while the fire-polished bead 17a is of some material advantage in enhancing the retentive capability of the finger grip 21 on the glass tube 11, fire-polishing without formation of a noticeable bead may be effected, as by employing a forming mandrel, to an acceptable extent of finger-grip sleeve retention capability.

Figures 2, 3:
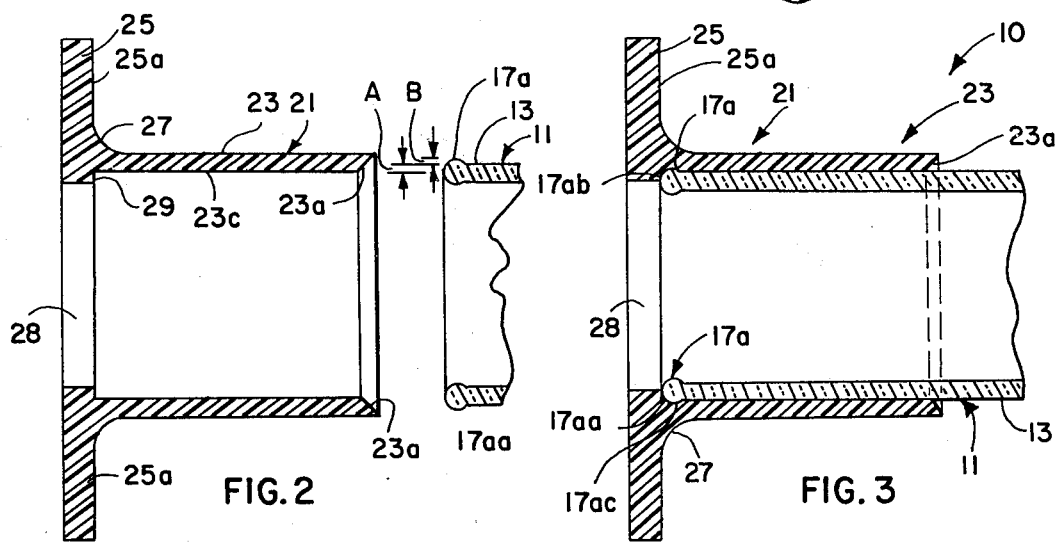
FIG. 2 is a longitudinal section view of the finger grip sleeve and the adjacent open end of the glass tube of FIG. 1, prior to assembly.
FIG. 3 is a longitudinal section view of the tube and finger grip assembly of FIG. 1.

The finger grip sleeve 21 is formed with a finger grip section 25 and a tubular sheath 23 which frictionally engages with the outer longitudinal surface of the glass tube 11. As is seen in FIG. 2, the tubular sheath section 23 of the finger grip sleeve 21 has an inner wall surface 23c which has a lesser radius than the outer radius of tubular wall 13 of glass tube 11, by an interference amount indicated by the reference character A, the increase in radius of the glass tube by the head 17a being indicated by the reference character B. Thus, the increase in diameter afforded by the bead 17a is 2B, and the diameter interference between the exterior diameter of the tube wall 13 and the tubular sheath inner wall surface 23c is 2A, according to the reference characters of this Figure. The interference value 2A is of substantial criticality in affording successful operations in accordance with the invention, particularly in light of the conventional practice of supplying glass tubing with a fairly wide tolerance range diameters from a nominal specified diameter, as practical utilization of the invention requires that the tubing either be utilized as directly supplied from the manufacturer or by internal sorting at some point prior to assembly use, to reduce the tolerance limits to an acceptable range. It has been found that the present invention may be practiced within the tolerance limits of glass tubing as such is conventionally supplied, according to one preferred inventive aspects and mode of practice, and according to a broader but substantially less desirable aspect and mode of practice by sorting the glass tubing and reducing the tolerance levels between the glass tubes of a given lot of tubing to an acceptable level for utilization according to this less desirable modified form of practicing the invention. Thus, the preferred embodiment of the invention in which the thermoplastic resin is preheated and is in a heated state during assembly, as will be later described may be practiced as applied to standard die-formed glass tubing and thermoplastic resin in the form of polypropylene, with glass tube tolerance levels of the order of approximately 0.034–0.035 inch diameter variations, of standard commercially supplied glass tubing of approximately 0.4 inch outer diameter as supplied in readily available commercial lots, and the modified and less desirable aspect of the invention may be practiced through the aid of sorting with tolerance for this diameter of glass tubing reduced to approximately 0.025–0.027 inch.

In addition, the bead 17a may be, for a given tolerance range, of greater consequence in the modified form of practice of the invention, and may be preferably held to a minimum, as of the order of 0.001–0.002 inch raised diameter increase for this and other practical considerations of use.

One or both of the end 17 of tube 11 and the facing end 23a of sheath 23 is formed with a cam surface which exerts a radially and circumferentially stretching action on the sheath 23 as a function of pressing of the sheat 23 axially against and onto the open end 17 of glass tube 11. As the glass tube 11 itself is essentially rigid as compared to the polypropylene sleeve 21, the camming action will result in the tube sheath 23 stretching in diameter and circumference and forming an elastically enlarged contiguous binding ring of substantial longitudinal extent about and along the longitudinal annular surface of tube 11 upon the complete pressing of the tubular sheath 23 of finger grip sleeve 21 onto the glass tube 11. This also sets up internal stresses in both the sleeve sheath 23 and the glass tube 11, which must be accommodated in practicing the invention.

This interference stretch-fit press-on of the finger strip sleeve 21 is preferably terminated by annular shoulder 29 forming a radially inward extension of the rear finger grip flange section of the finger grip sleeve 21. One preferred form of the shoulder 29 is illustrated, in which the shoulder 29 forms a through-bore 28 which is of at least as great a diameter as the effective internal diameter of the tube 11. This enables the ready insertion and removal of a conventional or other elastic plunger piston (not shown), as may be desired for ultimate use of this assembly, and also enables a plunger to be operated therethrough by external manual manipulation. Alternatively, the shoulder 29 may extend radially inwardly to form a through-bore 28 which may be of lesser diameter than the effective internal diameter of the glass tube 11, thereby affording a shoulder stop which will prevent or render difficult the removal of a plunger piston after insertion, as by insertion through the opposite end of the tube 11, and will likewise enable the through-bore 28 to be utilized for a manually operable plunger to be connected and/or removed therethrough.

Finger grip section 25 is formed in the illustrative and preferred embodiment as an integral flange having an enveloping annular portion including opposed extensions 25a and connecting side portions 25b. Other finger grip forms and constructions may be employed, including an annular flange having a constant diameter providing a round flange periphery, or the finger grip section may have integral molded finger gripping rings, or other suitable finger grip elements or elements. However, the illustrative embodiment is preferred, and particularly in employing a fully annular enveloping flange portion extending laterally beyond the outer diameter of the sheath 23 and enabling the employing annular fillet enlargement 27, particularly in the embodiments employing a fire-polished head 17a on the end of the glass tube 11.

As previously stated, one or both of the end 17 of tube 11 and end 23a of sheath 23 is formed with a cam surface which effects a circumferential and diameter stretching action on the sheath 23 as a function of pressing of the sheath 23 axially against and onto the open end of glass tube 11. A cam surface on the end of finger grip sleeve sheath 23 may be formed as an annular bevel cam surface 23a, as shown, which may have an outer edge blunting bevel 23b, if desired, or which may be omitted if outer edge blunting is not desired. Alternatively, the surface 23a, 23b, may be rounded or otherwise arcuately smoothly curved as viewed in longitudinal section, to provide the desired camming surface action with the end 17 of glass tube 11. Glass tube end 17 preferably fire-polished to form a smooth radially outer end edge surface 17aa, which preferably forms a small bead of approximately 0.001–0.005 inch added diameter, and which bead will normally extend beyond the nominal cylindrical diameter of the tube 11 both radially outwardly and radially inwardly, as well as providing the desired convex arcuate outer cam surface 17aa for camming interengagement with the interfacing end edge of sheath 23. (In this respect it will be appreciated that the drawings are largely schematic and that various parts or elements, such as bead 17a, have been exaggerated for purposes of illustration and clarity.) This small annular fire-polished bead serves a desired multiple purpose of cam stretching of the sheath as it is press-fit in enveloping interference fit over the end 17 and onto the longitudinal straight wall surface 13 of tube 11, as well as providing added retentive gripping effect and adding strength to the glass tube at the end 17. The glass tube end 17 may alternatively be ground or otherwise formed with a beveled or rounded outer end edge surface corresponding to surface 17aa, which may enable effecting of the desired cam action on the sheath 23. Also alternatively, the sheath 23 may have its initially interfacing end edge blunt, without the highly desired dual camming provided by both bevel 23a and bead 17a, although it will be appreciated that a sharp outer annular edge surface on the tube 11 is not desirable in any event as such will ordinarily effect a scraping and material-removal action in attempting to insert the tube into the sheath 23, with consequent difficulty in assembly and reduction in retentive resistance of the sheath on the tube.

The fillet 27 forms an integral smoothly connecting annular corner between annular sheath 23 and annular finger grip flange section 25. Fillet 27 serves also as an effectively elastic smoothly enlarged diameter reinforcement for the sheath 23 at the zone where the sheath 23 overlies the bead end 17a of tube 11. This smooth enlargement provided by the fillet 27 provides added strength and desirable lateral stress distribution in this zone, while enabling the sheath to adequately stretch in diameter and stretch in diameter and compress in thickness, without the cracking of glass tube 11 that might be caused by bottoming or terminating the glass tube end 17 in a zone within the grossly circumferentially enlarged and more rigid zone within the annular finger grip flange section 25, as well as enabling the material of the sleeve in the zone of fillet 27 to compensate for the added thickness of diameter of bead 17a and the expansion of sheath 23 necessary for the accommodation of the basic interference fit formed between the straight-walled section 13 of tube 11 with sheath 23 in this end overlie and flange grip connecting inner connection transition zone 27.

The invention has been applied in practical form to available glass tubing and employing polypropylene resin sold by Rexall, the utilized polypropylene resin being a heat-stabilized grade marketed as Rexall PP-13S, 12 melt index. Glass tubing of a nominal cylindrical wall 13 of 0.414 inch, with a conventionally supplied tolerance range in diameter of approximately 0.034 inch, has been suitably utilized according to the preferred aspect of the invention. In this respect the thickness of sheath 23 may be suitably of the order of approximately 0.020–0.040 inch, and preferably to the range of 0.030–0.035 inch, the length of the sleeve sheath 23 being within the range of approximately 0.4–0.7 inch in order to afford an adequate seated interference retention fit longitudinal extent between the sheath 23 and tube 11. The cylindrical inner wall 25c of sheath 23 may be very slightly tapered inwardly therealong from its open end adjacent annular beveled edge 23a, to the zone adjacent shoulder 29, as of the order of approximately 0.002 inch diameter change. The fillet enlargement may have a radius of approximately 0.025–0.250 inch and preferably is in the range of approximately 0.100 inch for these sizes of sleeves and tubes. Glass tubes of the order of 0.020–0.040 inch or greater may suitably be employed, using available commercial grades of glass, although tubing wall thickness of the order of as low as 0.010–0.015 inch may be utilized when employing high-strength glass for the glass tube 11. However, the smaller wall thicknesses are normally difficult to form and handle in other respects, and will not normally be desirable or necessary.

The indicated tolerance range which is available on a commercial basis from manufactures of die-formed glass tubing, namely approximately 0.034 inch, may be suitably accommodated according to the invention by practicing the preferred mode assembly of the tube 11 and sleeve 21. In this preferred mode of assembly, the sleeve 21, which may be conventionally injection-molded, is first preheated prior to assembly to an elevated temperature and substantially above normal ambient room temperature, and the sleeve 21 is assembled with the glass tube 11 while the sleeve 21 is at such elevated temperature. It has been found suitable to heat the sleeves 21 to an elevated temperature of the order of approximately 100°–160°F, although it is believed that temperatures within a range of values slightly below and substantially above this temperature range may suitably be employed, dependent to an extent upon the tolerance limits which must be accommodated in glass tubing sizes, it being appreciated that the upper temperature should not reach the tacky temperature zone for the polypropylene resin forming the sleeve 21. It has been found that by employing this preheating of the sleeve 21 and assembly of such with the glass tube 11 while in an elevated temperature condition, the range of interference tolerance which may be operably acceptable, between the internal diameter of the sheath 23 and its inner surface 23c and the normal outer wall diameter along the straight cylindrical wall section 13 of tube 11, may be substantially extended to accommodate commercial tolerance ranges of glass tubing, without requiring sorting. Thus, as noted, tolerance ranges of the order of approximately 0.034 inch for the outer diameter of glass tubing 11 of approximately 0.4 inch nominal outer diameter, may be accepted and used direct, without requiring sorting, while still providing adequate crack resistance of the polypropylene sleeve 21, and without causing cracking of the glass tubing 11, either during, immediately after, or after long-term storage of, the assembly 11, 21.

The invention may also be practiced by assembling the sleeve 21 onto the glass tube 11 while both are at the normal ambient room temperatures; however, the maximum acceptable interference fit in this less desired mode of practice of the invention has been found to be approximately 0.030 inch, and the range of tolerances which may be accommodated in the outer diameter of the glass tubing is substantially reduced, and will be of the order of approximately 0.025–0.027 inch, as the lower limit acceptable interference fit is approximately 0.003–0.005 inch, as distinguished from the substantially wider interference fit tolerance range extending from a lower limit of approximately 0.003–0.005 inch to an upper limit of approximately 0.037–0.039 inch which has been found to be operable for the preferred heated sleeve mode of assembly as discussed above. In addition, in the less desired mode of practice in which sleeve 21 is assembled cold, substantial residual stresses do remain in the sleeve 21 to an extent that such may, particularly after a long-term storage, result in cracking of the sleeve 21 along the sheath where the outer extent of the interference tolerance zone of approximately 0.030 inch is required or approached for a particular sorting utilization of glass tubing.

In a particular illustrative embodiment which utilizes glass tubing of nominal 0.414 inch outer diameter along the surface of the straight cylindrical wall section 13, and which was supplied within a specified commercial tolerance range of 0.401–0.435 inch, a finger grip sleeve 21 has been employed for a sheath inner diameter of approximately 0.398 inch at its entrance end and approximately 0.396 inch adjacent shoulder 29, utilizing the preferred preheated sleeve assembly method, as it will be noted that the resulting range of tolerance lies within the acceptable range of interference fit. The same nominal glass tube diameter of 0.414 inch may also be used in the less desired cold assembly method, with approximately the same inner wall 23c diameter for the sheath 23, by reducing the tolerance range of the glass tubing to within the acceptable tolerance of approximately 0.025–0.027 inch. In this illustrative embodiment, the sheath 23 has a total length of approximately 0.6 inch, and the fillet 27 has a radius of curvature of approximately 0.100 inch, with the finger grip flange section 25 having a longitudinal thickness of approximately 0.06 inch, and an outer flange extension diameter of approximately 0.9 inch. In this illustrative embodiment the shoulder 29 has been formed with an inner through-bore 28 diameter of approximately 0.314–0.317 inch.

Glass tube and finger grip assemblies 11, 21 constructed within the foregoing range have been found to provide pull-off resistance within the range of approximately 5 to 35 pounds, when the glass tube 11 is in a clean condition without lubricant such as silicone thereon. When the glass tube 11 has coating thereon, as may sometimes be desirable for other operational conditions such as the subsequent insertion of a plunger piston or slidable plug in the glass tube, the retentive resistance formed by the interference fit between the sleeve 21 and the glass tube 11 has been found to be reduced by the order of approximately 20 percent, and accordingly the lower range of interference tolerances may not be acceptable for a given required use where the retentive force required for utilization of the assembly in a given instance may be greater than the retentive resistance afforded by this lower range of tolerance fit. Such deficiency may be overcome by sorting, or otherwise insuring that the interference fit is sufficient to provide the desired retentative resistance to pull-off of the sleeve 21 from the glass tube 11.

Figure 4:
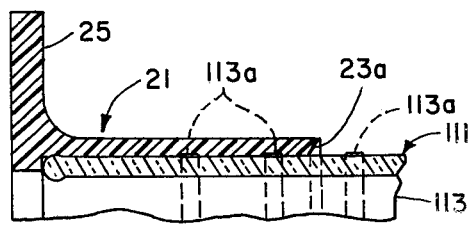
FIG. 4 is a longitudinal fragmentary section view of a modification according to the invention.

A modified form of practice of the invention is illustrated in FIG. 4, in which the glass tube 111 has raised spaced protrusions 113a on its surface, as may be provided by printing of graduations, legends, etc., on the glass tube 11 prior to assembly with the sleeve 21. This printing may be formed as by application of epoxy ink which is subsequently cured in situ on the glass tube or by the application of ceramic ink subsequently fired in place on the glass tube, the utilization of such inks to form graduations and other indicia being commonly and readily understood in the art, and such will accordingly not be further described herein, other than to note that such may suitably provide a raised added wall thickness and enlargement of the order of approximately 0.001–0.002 inch. As will be noted from FIG. 4, there raised surface segments 113a lie beneath the sheath 123 of finger grip sleeve 21, and afford additional retentive resistance to the removal of the finger grip flange in the course of usage of the assemblies 111, 121. While depressions may also be formed in the glass tube outer wall surface, for added retentive resistance, untempered scoring to form such depressions is not desirable as the glass is subsequently weakened along such score lines, which may result in subsequent cracking during or after assembly.

Figure 5:
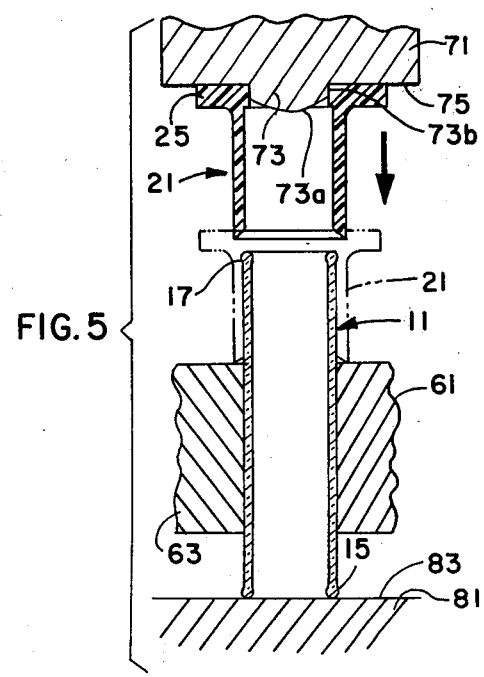
FIG. 5 illustrates the method of assembly of the arrangement of FIG. 1.

The assembly of the finger grip sleeve 21 onto the glass tube 11 is illustrated in FIG. 5, in which a work holder 71 having a gripping nipple 73 with a tapered nose 73a and cylindrical gripping surface 73b engages in releaseable frictional holding relation with bore-forming surface of shoulder 29, and in which glass tube 11 is held in a suitable guide chuck 61 which may be suitable by a V-chuck, with the glass tube either vertical or horizontal and further utilizing a backing member 31 for the opposite tube end 15. The work holder is moved downwardly to the glass tube 11 to move the sleeve sheath 23 into end contact with and into cam stretch-fitted interference gripping relationship about relatively long extent of the glass tube 11, the force required for this being transmitted through the forward face 75 of work holder 71. After completion of assembly, the assembly 11, 21 may be released from the initial frictional retentive engagement between gripping nipple surface 73b and the wall surface of through-bore 28, and the entire procedure may be repeated with a succeeding glass tube and finger grip sleeve.

While the invention has been illustrated and described with respect to various preferred and other embodiments and modes of practice thereof, it will be appreciated that various modifications may be made without departing from the scope and spirit of the invention. Accordingly, the invention is not to be limited by the illustrative embodiment but only by the scope of the appended claims.

I claim:

1. A glass tube and non-glass finger grip arrangement for use particularly in packaging and subsequent dispensing of chemicals, comprising a length of substantially constant diameter die-formed glass tube having a peripheral wall with a die-formed bore and outer annular surface, the diameters both of which bore and outer annular surface are each at least several times the thickness of said peripheral wall whereby said glass tube is thin-walled relative to both its outer and bore diameters, and a sleeve of thermoplastic resin having a laterally extending finger-grip protrusion integrally formed thereon, said sleeve having an annularly substantially continuous substantially constant diameter inner bore wall in solely friction-retained engagement in a stretched-fit friction-retained state over and along one end of said glass tube, the diameters of both the bore and the outer annular surface of said glass tube being at least several times the wall thickness of the longitudinally extent of said sleeve extending over and along said glass tube.

said tube having raised surface projections on the outer annular surface beneath and contiguous with the inner surface of said sleeve, said surface projections being of substantially smaller radial thickness than the adjoining overlying portion of said sleeve.

2. An arrangement according to claim 1, said surface projections being bonded printing on the outer surface of said glass tube.

3. An arrangement according to claim 1, said surface projections being graduations formed on said glass tube.

4. An arrangement according to claim 1, said projections being superimposed lines of fine glass particulate fused to said glass tube surface.

5. An arrangement according to claim 4, said projections being superimposed lines of cured resin adhered to said glass tube surface.

* * * * *